United States Patent [19]

Brown

[11] Patent Number: 4,990,648
[45] Date of Patent: Feb. 5, 1991

[54] PROCESS FOR PRODUCING AN ALKYLTHIOBENZOATE

[75] Inventor: Richard W. Brown, Richmond, Calif.

[73] Assignee: ICI Americas Inc., Wilmington, Del.

[21] Appl. No.: 460,432

[22] Filed: Jan. 3, 1990

Related U.S. Application Data

[62] Division of Ser. No. 290,018, Dec. 22, 1988, Pat. No. 4,925,970.

[51] Int. Cl.$^5$ .................... C07C 321/28; C07C 69/75
[52] U.S. Cl. ...................................... 560/18; 560/125; 562/432; 562/507
[58] Field of Search .................. 560/18, 125; 562/507, 562/432

[56] References Cited

U.S. PATENT DOCUMENTS

| | | | |
|---|---|---|---|
| 2,173,827 | 9/1939 | Donleavy | 560/18 |
| 3,236,875 | 2/1966 | Reifschneider | 560/18 |
| 3,825,549 | 7/1974 | Yale et al. | 560/18 X |
| 4,692,545 | 9/1987 | Carter | 560/18 |
| 4,704,467 | 11/1987 | Wehrenberg | 560/11 |

FOREIGN PATENT DOCUMENTS

| | | |
|---|---|---|
| 2073393 | 10/1971 | France . |
| 574897 | 4/1976 | Switzerland . |
| 595783 | of 1947 | United Kingdom . |

OTHER PUBLICATIONS

Ladika et al., *J. Org. Chem.* vol. 50, pp. 4544–4548 (1985).
Begbie et al., *J. Chem. Soc., Perkin Trans. I*, pp. 602–605 (1977).
van der Veen et al., *J. Chem. Soc. Perkin Trans.* I. pp. 661–668 (1985).
Chinoin Gyogyszer, CA 44:4047i, (1949).
Kendall et al., CA 42:4763i, (1947).
Akiyama, *Bull. Chem. Soc. Japan*, vol. 50, pp. 936–938, (1977).
Mukaiyama et al., *Chemistry Letters*, pp. 479–482, (1973).
Campaigne et al., *J.A.C.S.*, vol. 76, pp. 1272–1275, (1954).
Romo et al., *J.A.C.S.*, vol. 73, pp. 1528–1533, (1951).
Rosenkranz et al., *J.A.C.S.*, vol. 71, pp. 3689–3694, (1949).
Seitz et al., *Arch. Pharm.*, No. 315, pp. 169–174, (1982).

*Primary Examiner*—Paul J. Killos
*Assistant Examiner*—Vera C. Clarke
*Attorney, Agent, or Firm*—Joel G. Ackerman

[57] ABSTRACT

A process for production of an alkylthiobenzoate comprising reacting a cyclohexenone having the formula

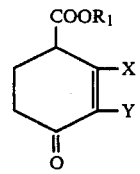

in which $R_1$ is $C_1$–$C_6$ alkyl; X is alkyl or unsubstituted alkyl; and Y is hydrogen, halogen or alkyl, with a mercaptan having the formula $R_2SH$ in which $R_2$ is $C_1$–$C_4$ alkyl, preferably in the presence of an acid catalyst, to form a cyclohexadiene thioether, and dehydrogenating the thioether to produce a thioalkylbenzoate.

The thioalkylbenzoate may be further converted by oxidation and/or hydrolysis to a corresponding thioalkyl, alkylsulfinyl or alkylsulfonyl benzoic acid.

11 Claims, No Drawings

PROCESS FOR PRODUCING AN ALKYLTHIOBENZOATE

This is a divisional of application Ser. No. 290,018, filed Dec. 22, 1988, now U.S. Pat. No. 4,925,970.

This invention involves a novel process for producing 2-alkyl- and 2-(substituted alkyl)-4-alkylthio- and alkylsulfonyl-benzoic acids and their derivatives, particularly their esters. More specifically it relates to a process for producing such esters from a non-aromatic compound, followed by conversion of the ester to the benzoic acid, if the latter is the desired product. As will be discussed below, this invention involves several processing steps and includes novel intermediates.

In general, the products produced by this invention have the formula

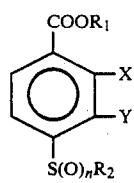
(I)

in which $R_1$ is hydrogen or alkyl; $R_2$ is an alkyl group which may be the same as or different from $R_1$; X is alkyl or substituted alkyl; Y is hydrogen, halogen or alkyl; and n is 0, 1 or 2.

The alkyl groups in compounds of this type, and the intermediates through which they are prepared, will generally contain from 1 to 6, preferably from 1 to 4, carbon atoms. Preferred substituents include:

for $R_1$—hydrogen and all $C_1$-$C_4$ alkyl groups, i.e., methyl, ethyl, n-propyl, isopropyl, n-butyl, sec-butyl, isobutyl and tertiary butyl;

for X—methyl, ethyl and $C_1$-$C_2$ haloalkyl, particularly trifluoromethyl;

for Y—hydrogen, $C_1$-$C_4$ alkyl (particularly methyl and ethyl) and chlorine;

for $R_2$—all $C_1$-$C_4$ alkyl groups as for $R_1$; and for n—0 and 2.

Compounds of this type in which $R_1$ is an alkyl group (i.e., esters of a substituted benzoic acid) are produced according to the process of this invention from a non-aromatic starting material as follows.

In the first step, a 4-carboalkoxy-2-cyclohexen-1-one is reacted with a mercaptan, particularly an alkyl mercaptan, to produce a thioether of a cyclohexadiene.

In the second step, the cyclohexadiene thioether is dehydrogenated to produce the corresponding thioalkylbenzene compound.

If an alkylsulfonyl substituted compound is the desired product, the product of the second step is contacted with an oxidizing agent so as to oxidize the thioalkyl group to an alkylsulfonyl group. Alternatively, if an alkylsulfinyyl compound is the desired product, the thioalkyl group may be partially oxidized to the alkylsulfinyl group ($SOR_2$). Finally, if the benzoic acid is desired, the ester of the alkylthio, alkylsulfinyl or alkylsulfonyl acid can be converted to the free acid by hydrolysis.

The process as described above utilizes as a starting material a carboalkoxy cyclohexenone, particularly a 4-carboalkoxy-2-cyclohexen-1-one which has the general formula

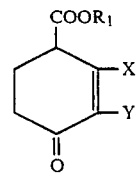
(II)

in which $R_1$ is an alkyl group having from 1 to 6 carbon atoms, preferably from 1 to 4 carbon atoms, X is $C_1$-$C_4$ alkyl or substituted alkyl and Y is hydrogen, $C_1$-$C_4$ alkyl or halogen. Two of the most common examples of such compounds are known by the terms Hagemann's ester and 2-ethyl-Hagemann's ester. These are compounds in which respectively $R_1$ is ethyl, X is methyl and Y is hydrogen (Hagemann's ester) and $R_1$ is ethyl, X is methyl and Y is ethyl (2-ethyl Hagemann's ester).

Specific compounds of formula (II) which may not be commercially available may be prepared by methods such as those described by Begbie et al., *J. Chem. Soc., Perkin Transactions I*, 602 (1972), using appropriate starting materials.

In the first step of this process a compound having the formula

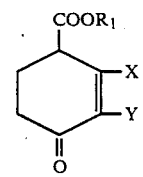
(II)

is reacted with a mercaptan, preferably an alkyl mercaptan having the formula $R_2SH$ in the presence of an acid catalyst and a solvent, at a temperature of between about −40° C. and about 60° C., preferably between about 0° C. and 30° C. The crude product from this reaction is preferably heated in an aromatic solvent such as mesitylene to drive the reaction to completion. In this step the starting material is converted into a thioalkyl substituted cyclohexadiene having the general formula

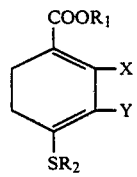
(III)

Cyclohexadienes of this formula are novel and form one feature of this invention.

The acid catalyst utilized in this step of the process is preferably p-toluenesulfonic acid, but other acid catalysts which can promote this reaction may be employed, for example, titanium tetrachloride, zinc chloride, aluminum chloride, pyridine hydrochloride, phosphorus pentoxide, or anhydrous hydrogen chloride. The acid catalyst is generally used in an amount of from about 1 to about 15 mole percent, preferably from about 1 to about 5 mole percent, based on the cyclohexenone. The solvent employed is preferably an alcoholic solvent such as methanol or ethanol.

In the next step, the cyclohexadiene is dehydrogenated to the corresponding thioalkyl benzoate

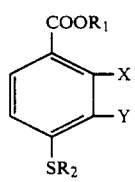

(IV)

with a suitable dehydrogenation agent, including N-bromosuccinimide, 2,3-dichloro-5,6-dicyanobenzoquinone (DDQ), palladium supported on carbon or sulfur in the presence of quinoline. Thus, in two relatively simple steps, a thioalkyl-substituted benzoate is produced from a non-aromatic substance.

The thioalkylbenzoate (IV) produced in the second step of this process may be used as an intermediate for various purposes, including production of pesticides and general organic chemical syntheses of various benzene derivatives. If desired, the thioalkylbenzoate may be converted to the corresponding benzoic acid by hydrolysis. Alternatively, the thioalkyl group may be oxidized to an alkylsulfinyl or alkylsulfonyl group by treatment with a suitable oxidizing agent. For instance, if oxidation to an alkylsulfonyl group is desired the thioalkylbenzoate may be contacted with a suitable oxidizing agent such as peracetic acid, sodium hypochlorite, or m-chloroperbenzoic acid to produce the corresponding alkylsulfonylbenzoate

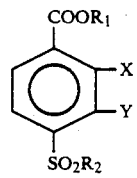

(V)

which, if desired, may be converted to the free acid

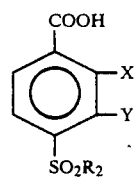

(VI)

by hydrolysis.

The invention is illustrated by the following examples.

EXAMPLE 1

Production of 1-Carbethoxy-2-methyl-4-methylthio-1,3-cyclohexadiene

In a flask were placed 500 grams (g) (2.75 mol) of 4-carbethoxy-3-methyl-2-cyclohexen-1-one, 45 g (0.24 mol) of p-toluenesulfonic acid and 3.0 liters (L) of ethanol. The reaction mixture was cooled to 10° C.; then 300 g (6.25 mol) of methanethiol was added over 4.25 hours.

The reaction mixture was allowed to stand overnight, diluted with 1.5 L of toluene and then washed with 2 L of water. The organic phase was dried and concentrated in vacuo to give 686 g of a yellow liquid. At this point, analysis by gas chromatography showed no residual starting cyclohexenone. The yellow liquid was heated in 2.5 L of mesitylene under reflux for 3 hours.

The mesitylene was stripped off, leaving 660 g of a gold liquid, which was shown by gas chromatography to be 85% desired product.

EXAMPLE 2

Dehydrogenation

1-Carbethoxy-2-methyl-4-methylthio-1,3-cyclohexadiene was converted to dehydrogenation to the corresponding alkylthio compound, ethyl 2-methyl-4-(methylthio)benzoate as follows.

Eight hundred forty-eight grams (848 g) (3.4 mol) of the cyclohexadiene was added to a flask containing 781 g (3.4 mol) of 2,3-dichloro-5,6-dicyanobenzoquinone (DDQ) in 4 L benzene. The resulting mixture was heated at reflux for 5 hours. The resulting slurry was filtered through alumina and the filtrate concentrated in vacuo to give 712 g of a dark liquid. Gas chromatographic analysis showed 86% of the desired ester.

EXAMPLE 3

Oxidation to alkylsulfonylbenzoate 1.77 6ram (8.42 mmol) of ethyl 2-methyl-4-(methylthio)benzoate was placed in a flask, together with 35 mL of dichloromethane. The mixture was cooled to 3° C. There was then added 5.8 g (38.4 mmol) of 40% peracetic acid. The mixture was stirred with temperature maintained at below 10° C.

The reaction product was neutralized with sodium bisulfite and the pH adjusted to a value of 12 with 5% aqueous sodium hydroxide. The mixture was then extracted twice with 150 mL portions of dichloromethane, dried and the solvent removed by stripping. There was obtained 1.56 g (78% of theoretical yield) of a clear yellow oil, shown by gas chromatographic analysis to be 89 area percent of the desired product. The structure was confirmed by spectroscopic analyses.

EXAMPLE 4

Production of 2-Methyl-4-(methylsulfonyl)benzoic acid

The product of Example 3 was hydrolyzed to the corresponding benzoic acid using 10.73 mmol of sodium hydroxide (5% aqueous solution) in methanol, followed by treatment with 0.6N hydrochloric acid. There was obtained 0.87 g (76% of theoretical yield) of a white solid whose structure was confirmed as the desired product by spectroscopic analyses.

What is claimed is:

1. A process for production of an alkylthiobenzoate having the formula

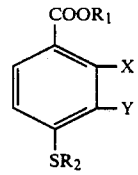

in which $R_1$ is $C_1$–$C_6$ alkyl; $R_2$ is $C_1$–$C_4$ alkyl; X is $C_1$–$C_4$ alkyl or $C_1$–$C_4$ haloalkyl; and Y is hydrogen, halogen or $C_1$–$C_4$ alkyl, comprising the steps of (a) reacting a cyclohexenone having the formula

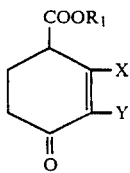

with a mercaptan having the formula $R_2SH$ to produce a cyclohexadiene thioether having the formula

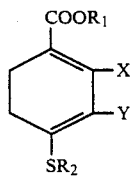

and (b) dehydrogenating the product of step (a).

2. A process according to claim 1 in which step (a) is conducted in the presence of from about 1 to about 15 mol percent of an acid catalyst, based on the cyclohexenone.

3. A process according to claim 2 in which the acid catalyst is p-toluenesulfonic acid.

4. A process according to claim 1 in which $R_1$ is $C_1$-$C_4$ alkyl; X is methyl, ethyl or trifluoromethyl; and Y is hydrogen, chlorine or $C_1$-$C_4$ alkyl.

5. A process according to claim 4 in which X is trifluoromethyl and Y is hydrogen.

6. A process according to claim 4 in which X is methyl and Y is chlorine.

7. A process according to claim 4 in which X is methyl and Y is hydrogen.

8. A process according to claim 4 in which X is methyl and Y is ethyl.

9. A process according to claim 1 further comprising reacting the product of step (b) with an oxidizing agent to oxidize the thioalkyl group to an alkylsulfonyl group.

10. A process according to claim 9 additionally further comprising hydrolyzing the alkylsulfonyl benzoate to the corresponding benzoic acid.

11. A compound having the formula

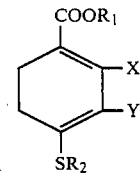

in which $R_1$ is $C_1$-$C_6$ alkyl; $R_2$ is $C_1$-$C_4$ alkyl; X is $C_1$-$C_4$ alkyl or $C_1$-$C_4$ haloalkyl; and Y is hydrogen, halogen or $C_1$-$C_4$ alkyl.

* * * * *